US008361292B2

(12) United States Patent
Nakayama et al.

(10) Patent No.: US 8,361,292 B2
(45) Date of Patent: Jan. 29, 2013

(54) METHOD FOR ANALYZING HEMOGLOBIN BY CAPILLARY ELECTROPHORESIS AND ADDITIVE USED THEREIN

(75) Inventors: Yusuke Nakayama, Kyoto (JP); Satoshi Yonehara, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 353 days.

(21) Appl. No.: 12/514,293

(22) PCT Filed: Apr. 23, 2008

(86) PCT No.: PCT/JP2008/057825
§ 371 (c)(1),
(2), (4) Date: May 8, 2009

(87) PCT Pub. No.: WO2008/136321
PCT Pub. Date: Nov. 13, 2008

(65) Prior Publication Data
US 2010/0032294 A1    Feb. 11, 2010

(30) Foreign Application Priority Data

Apr. 27, 2007  (JP) ................................ 2007-119259

(51) Int. Cl.
*G01N 27/447*  (2006.01)
(52) U.S. Cl. ....................................... 204/451; 204/601
(58) Field of Classification Search .......... 204/450–470, 204/546–550, 600–621, 641–645
See application file for complete search history.

(56) References Cited

U.S. PATENT DOCUMENTS
5,599,433 A * 2/1997 Keo et al. ...................... 204/451
(Continued)

FOREIGN PATENT DOCUMENTS
CN    1239424    12/1999
JP    9-105739   4/1997
(Continued)

OTHER PUBLICATIONS

Bo Huang, Hongkai Wu, Samula Kim and Richard N. Zare, Coating of poly(dimethylsiloxane) with n-dodecyl-β-D-maltoside to minimize nonspecific protein and adsorption, Lab Chip, Sep. 5, 2005, 5, 1005-1007.*

(Continued)

*Primary Examiner* — Luan Van
*Assistant Examiner* — Maris R Kessel
(74) *Attorney, Agent, or Firm* — Morgan, Lewis & Bockius LLP

(57) ABSTRACT

The present invention provides a method for analyzing hemoglobin by capillary electrophoresis, that allows the apparatus to be smaller in size, allows a highly precise analysis to be obtained, and allows the analysis to be performed in a short period of time. The analytical method of the present invention are methods for analyzing hemoglobin by capillary electrophoresis, comprising: a sample-providing step of providing a sample containing hemoglobin; a capillary tube-providing step of providing a capillary tube containing a buffer solution; and an electrophoresis step of carrying out electrophoresis of the sample, by introducing the sample into the buffer solution in the capillary tube, and applying a voltage across both ends of the capillary tube; wherein the electrophoresis is carried out following at least one of modes (A) and (B) below: (A) the electrophoresis is carried out with a surfactant (a) added to the buffer solution, the surfactant (a) being a non-ionic surfactant having an alkyl group as a hydrophobic portion and a sugar as a hydrophilic portion; and (B) the electrophoresis is carried out with a surfactant (b) added to the sample, the surfactant (b) being a betaine-type amphoteric surfactant.

9 Claims, 10 Drawing Sheets

Time(min)

U.S. PATENT DOCUMENTS

| | | | |
|---|---|---|---|
| 2002/0032133 A1 | 3/2002 | Schelges et al. | 510/119 |
| 2004/0256232 A1* | 12/2004 | Jiang et al. | 204/451 |
| 2005/0161332 A1* | 7/2005 | Vigh | 204/548 |
| 2010/0006436 A1 | 1/2010 | Oishi et al. | 204/451 |

FOREIGN PATENT DOCUMENTS

| | | |
|---|---|---|
| JP | 11-223624 | 8/1999 |
| JP | 11-295286 | 10/1999 |
| JP | 2003-294752 | 10/2003 |
| JP | 2004-77457 | 3/2004 |
| JP | 2006-145537 | 6/2006 |
| JP | 2008-164382 | 7/2008 |
| JP | 2008-170351 | 7/2008 |
| JP | 2008-256460 | 10/2008 |
| JP | 2008-267819 | 11/2008 |
| JP | 2008-164382 | 7/2009 |
| JP | 2008-170350 | 7/2009 |
| WO | WO 2008/078781 | 7/2008 |
| WO | WO 2008/078781 | 7/2009 |

OTHER PUBLICATIONS

Pier Giorgio Righetti, Alessandra Bossi, Erna Olivieri, Cecilia Gelfi, Capillary electrophoresis of peptides and proteins in acidic, isoelectric buffers: recent developments, Journal of Biochemical and Biophysical Methods, vol. 40, Issues 1-2, Jul. 28, 1999, pp. 1-15.*

Doelman, J.A., Siebelder, C.W.M., Nijhof, W.A., Weykamp, C.W., Janssens, J. and Penders, T.J., Capillary electrophoresis system for hemoglobin A1c determinations evaluated, Clin. Chem. 43 (4) (1997), 644-648.*

F. Dang, K. Kakehi, J. Cheng, O. Tabata, M. Kurokawa, K. Nakajima, M. Ishikawa and Y. Baba, Hybrid, Hybrid Dynamic coating with n-dodecyl-β-D-maltoside and Methyl Cellulose for High-Performance Carbohydrate Analysis on Poly(methyl methacrylate) Chips, Anal. Chem. 2006, 78 (1452-2458).*

Office Action issued Oct. 25, 2011 in corresponding Chinese Patent Application No. 200880000931.4 (English language translation included).

* cited by examiner

METHOD FOR ANALYZING HEMOGLOBIN BY CAPILLARY ELECTROPHORESIS AND ADDITIVE USED THEREIN

The present application is a U.S. National Phase Application of International Application No. PCT/JP2008/057825, filed Apr. 23, 2008, which claims the benefit of Japanese Patent Application No. 2007-119259, filed Apr. 27, 2007, both of which are hereby incorporated by reference in their entirety.

TECHNICAL FIELD

The present invention relates to a method for analyzing hemoglobin by capillary electrophoresis and an additive used therein.

BACKGROUND ART

In capillary electrophoresis methods, ions that have gathered on the inner wall of a capillary tube migrate upon voltage application to generate an electroosmotic flow, which causes migration of a sample; thus, electrophoresis is carried out. Furthermore, hemoglobin (Hb) in blood reacts with glucose in the blood to become glycated Hb. The glycated Hb in the blood reflects the past history of the blood glucose level in a biological body and, therefore, is considered as an indicator in, for example, the diagnosis and treatment of diabetes. Among such glycated Hb, hemoglobin A1c (HbA1c) is measured by laboratory tests and the like as an especially important indicator. HbA1c is glycated at the beta chain N-terminal valines. Also, hemoglobin S (HbS) is a molecule that causes sickle cell anemia, and so is important in diagnosis. In HbS, the 6th glutamic acid (Glu) in the beta chains is substituted with valine (Val). Accordingly, there is a demand for a technique for precisely analyzing various hemoglobins, such as HbA1c and HbS. Examples of methods for measuring hemoglobin in blood include agarose electrophoresis methods, capillary electrophoresis methods, HPLC methods, immunological methods, enzymatic methods, and the like. Among these, those allowing minute variations such as genetic variants of hemoglobin to be detected are capillary electrophoresis methods and HPLC methods. Furthermore, an apparatus for analyzing hemoglobin is required to be relatively small in size. With respect to this point, it is difficult to reduce the size of the whole apparatus in HPLC methods. On the other hand, capillary electrophoresis methods allow the size of the whole apparatus to be reduced, with the apparatus being formed into a microchip.

However, the precision of the analyses of various hemoglobins is insufficient in conventional capillary electrophoresis methods. With respect to this point, as a technique for precisely analyzing HbA1c, there is a technique in which the inner wall of a capillary tube is coated with a protein, which is then coated with a polysaccharide (Patent Document 1) (hereinafter, referred to as a "conventional technology (1)"). However, conventional technology (1) is problematic in that normal hemoglobin (HbA0) and HbS cannot be separated, and their peaks overlap. The fact that HbA0 and HbS cannot be separated means that the ratio of HbA1c in blood cannot be measured accurately. That is to say, conventional technology (1) is problematic in that the measured HbA1c of a patient suffering from sickle cell anemia is artificially low. As a method for solving this problem, there is a method in which capillary electrophoresis is carried out with a zwitterionic type of running buffer that is allowed to contain a flow inhibitor such as aliphatic diamine, where the inner wall of the capillary tube is not coated (Patent Document 2) (hereinafter, referred to as a "conventional technology (2)"). However, the conventional technology (2) needs a long period of time (e.g., 10 minutes) for measurement. Accordingly, conventional technology (2) cannot be applied substantially to laboratory tests in which many samples are required to be processed in a short period of time. Furthermore, in conventional technology (2), a long capillary tube is required. Thus, when using conventional technology (2), the apparatus cannot be made smaller. Moreover, in conventional technology (2), HbA1c cannot be measured although HbA0 and HbS can be separated.

[Patent Document 1] JP 9(1997)-105739 A
[Patent Document 2] JP 2006-145537 A

DISCLOSURE OF THE INVENTION

It is an object of the present invention to provide methods for analyzing hemoglobin by capillary electrophoresis, that allows the apparatus to be relatively small in size, allows a highly precise analysis to be obtained, and allows the analysis to be performed in a short period of time, and an additive used in such methods.

In order to achieve the aforementioned object, analytical methods of the present invention are methods for analyzing hemoglobin by capillary electrophoresis, comprising:

a sample-providing step of providing a sample containing hemoglobin;

a capillary tube-providing step of providing a capillary tube containing a buffer solution; and an electrophoresis step of carrying out electrophoresis of the sample, by introducing the sample into the buffer solution in the capillary tube, and applying a voltage across both ends of the capillary tube;

wherein the electrophoresis step is carried out following at least one of modes (A) and (B) below:

(A) the electrophoresis step is carried out with a surfactant (a) added to the buffer solution; surfactant (a) is a non-ionic surfactant having an alkyl group as a hydrophobic portion and a sugar as a hydrophilic portion; and (B) the electrophoresis step is carried out with a surfactant (b) added to the sample; surfactant (b) is a betaine-type amphoteric surfactant.

An additive of the present invention is an additive for capillary electrophoresis used in the analytical method of the present invention, comprising at least one of surfactants (a) and (b), surfactant (a) is a non-ionic surfactant having an alkyl group as a hydrophobic portion and a sugar as a hydrophilic portion, and surfactant (b) is a betaine-type amphoteric surfactant.

The analytical methods of the present invention allow, for example, HbA0 and HbS to be analyzed separately, and the analysis time to be shorter than that in conventional examples. Furthermore, analytical methods of the present invention enable, for example, HbA1c to be analyzed precisely and the measured HbA1c to be prevented from being artificially low even in a blood sample from a patient suffering from sickle cell anemia. Furthermore, analytical methods of the present invention allow the length of the capillary tube to be shorter than that in conventional examples, which also allows the analysis apparatus to be smaller in size compared to those in conventional examples.

BEST MODE FOR CARRYING OUT THE INVENTION

Figure 1:
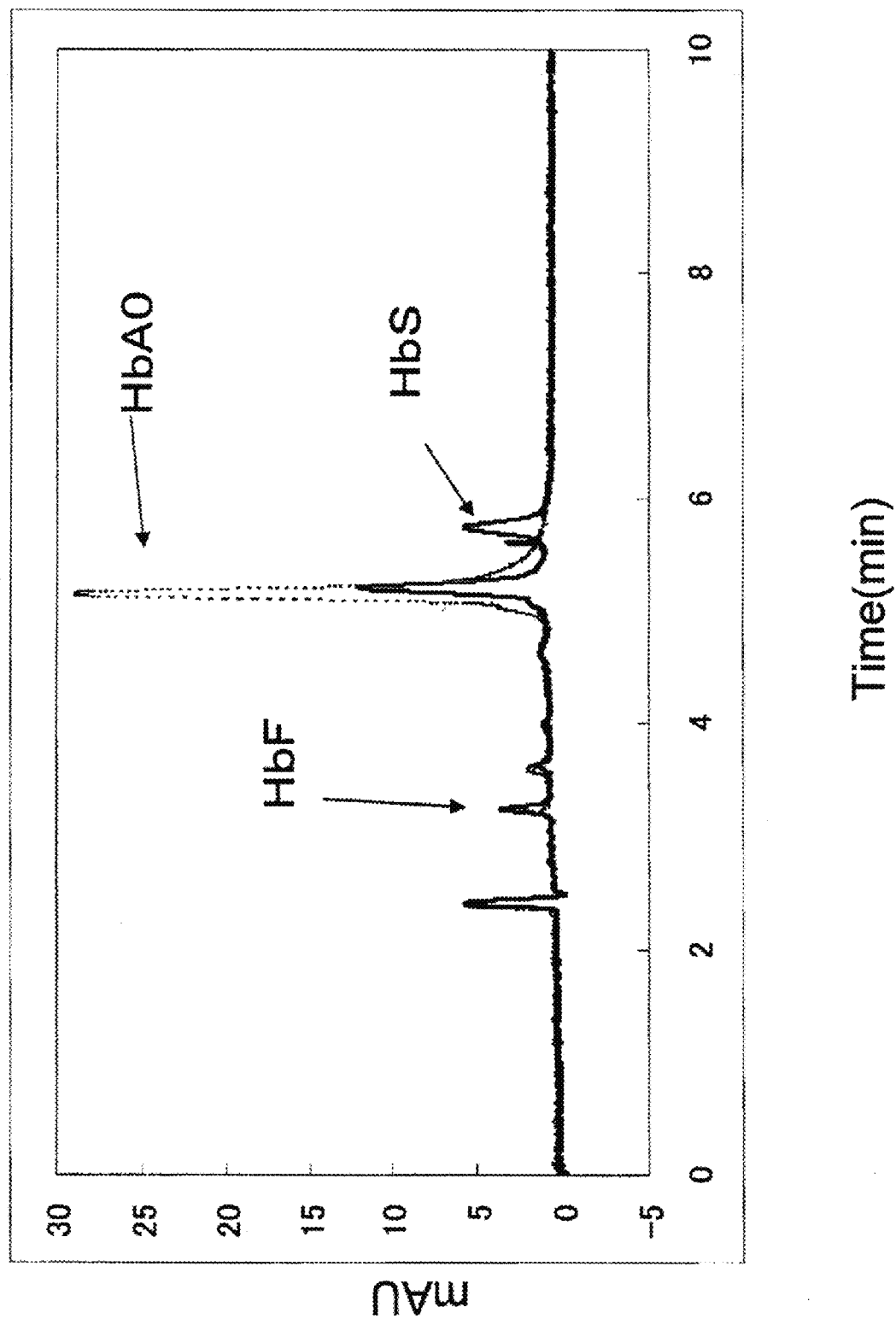
FIG. 1 shows electropherograms showing the results of an analysis of hemoglobin in an example of the present invention.

In mode (A) according to the present invention, preferably, surfactant (a) is added to the buffer solution in the capillary tube-providing step.

In surfactant (a) according to the present invention, preferably, the alkyl group has 11 to 16 carbon atoms, and the sugar is a monosaccharide or a disaccharide. More preferably, in surfactant (a) according to the present invention, the alkyl group is a linear alkyl group having 11 or 12 carbon atoms, and the sugar is a disaccharide.

In mode (B) according to the present invention, preferably, surfactant (b) is added to the sample in the sample-providing step.

Preferably, surfactant (b) according to the present invention is a sulfobetaine-type amphoteric surfactant.

In the analytical methods of the present invention, preferably, an anionic group-containing compound is added to the buffer solution, and a complex of the hemoglobin and the anionic group-containing compound is subjected to electrophoresis. In this case, preferably, the anionic group-containing compound is added to the buffer solution in the capillary tube-providing step. Preferably, the anionic group-containing compound is an anionic group-containing polysaccharide.

In the analytical methods of the present invention, preferably, HbA0 and HbS are separated.

In the analytical methods of the present invention, preferably, hemoglobin that is to be analyzed is at least one hemoglobin selected from the group consisting of HbA1c, HbS, HbC, HbM, HbH, and HbF.

Next, the present invention will be described by way of examples.

As described above, analytical methods of the present invention comprise a sample-providing step, a capillary tube-providing step, and an electrophoresis step. The capillary electrophoresis is carried out following at least one of the modes (A) and (B) below:

(A) the electrophoresis step is carried out with a surfactant (a) added to the buffer solution; surfactant (a) is a non-ionic surfactant having an alkyl group as a hydrophobic portion and a sugar as a hydrophilic portion; and (B) the electrophoresis step is carried out with a surfactant (b) added to the sample; surfactant (b) is a betaine-type amphoteric surfactant.

In the sample-providing step, a sample containing hemoglobin is provided. Examples of the sample containing hemoglobin include a hemolyzed sample obtained by hemolyzing whole blood. Examples of hemolyzation methods include ultrasonic treatments, freezing and thawing treatments, pressing treatments, osmotic pressure treatments, surfactant treatments, and the like. The hemolyzed sample may be diluted as appropriate, for example, with water, physiologic saline, buffer solution, or the like.

In mode (B), preferably, surfactant (b) is added to the sample in the sample-providing step, as described above. However, the present invention is not limited thereto. That is to say, surfactant (b) need only be added to the sample before the sample is introduced into the buffer solution in the capillary tube in the electrophoresis step.

As described above, surfactant (b) is a betaine-type surfactant. Examples of betaine-type surfactants include carboxybetaine-type surfactants and sulfobetaine-type surfactants. Among these, a sulfobetaine-type surfactant is preferable. Examples of the carboxybetaine-type surfactant include N,N-dimethyl-N-alkyl-N-carboxyalkylene ammonium betaine.

Examples of the sulfobetaine-type surfactant include N,N,N-trialkyl-N-sulfoalkylene ammonium betaine. The three alkyl groups are the same or mutually different. The number of carbon atoms of the alkyl group is, for example, 14 to 18. The alkyl group is a linear alkyl group or a branched alkyl group. The number of carbon atoms of the sulfoalkylene group is, for example, 1 to 3. Specific examples of the sulfobetaine-type surfactant include palmityl sulfobetaine.

The ratio of surfactant (b) added to the sample is, for example, 0.001 to 0.1 wt %, preferably 0.005 to 0.05 wt %, and more preferably 0.01 to 0.03 wt %, with respect to the total of the sample and surfactant (b).

The capillary tube-providing step is a step of providing a capillary tube into which the buffer solution has been injected.

The buffer solution is not particularly limited, but a buffer containing an acid used therein is preferable. Examples of the acid include maleic acid, tartaric acid, succinic acid, fumaric acid, phthalic acid, malonic acid, and malic acid. Preferably, the buffer solution contains a weak base. Examples of weak bases include arginine, lysine, histidine, tris, and the like. The pH of the buffer solution is, for example, 4.5 to 6. Examples of types of buffer solutions include MES, ADA, ACES, BES, MOPS, TES, HEPES, and the like.

Preferably, the anionic group-containing compound is added to the buffer solution, as described above. When the anionic group-containing compound is added, in the electrophoresis step, a complex of the anionic group-containing compound and the hemoglobin in the buffer solution is subjected to electrophoresis. Accordingly, the analytical precision is improved, the analytical time can be reduced, and the length of the capillary tube can be reduced.

Preferably, the anionic group-containing compound is an anionic group-containing polysaccharide. Examples of anionic group-containing polysaccharides include sulfated polysaccharide, carboxylated polysaccharide, sulfonated polysaccharide, and phosphorylated polysaccharide. Among these, sulfated polysaccharide and carboxylated polysaccharide are preferable. The sulfated polysaccharide is preferably, for example, chondroitin sulfate or heparin, and more preferably chondroitin sulfate. The carboxylated polysaccharide is preferably alginic acid or a salt thereof (e.g., sodium alginate). There are seven types of chondroitin sulfates A, B, C, D, E, H, and K and any of them may be used. In the buffer solution, the concentration of the anionic group-containing compound is, for example, 0.01 to 5 wt %.

In mode (A), preferably, surfactant (a) is added to the buffer solution in the capillary tube-providing step, as described above. However, the present invention is not limited thereto. That is to say, surfactant (a) need only be added to the buffer solution before the sample is introduced into the buffer solution in the capillary tube in the electrophoresis step.

As described above, surfactant (a) is a non-ionic surfactant having an alkyl group as a hydrophobic portion and a sugar as a hydrophilic portion. The alkyl group may be, for example, a linear alkyl group or a branched alkyl group, but a linear alkyl group is preferable. The number of carbon atoms of the alkyl group is, for example, 1 to 18, preferably 11 to 16, and more preferably 11 or 12. Specific examples of alkyl groups include methyl group, ethyl group, n-propyl group, isopropyl group, n-butyl group, isobutyl group, sec-butyl group, tert-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, and the like. The sugar may be a monosaccharide, a disaccharide, or a higher saccharide. The number of monosaccharides yielded is, for example, 1 to 20, preferably 1 to 3, and more preferably 2. Specific examples of surfactant (a) include dodecyl-D-maltoside, sucrous monolaurate, oxatridecyl-D-mannoside, undecyl maltoside, octyl glucoside, sucrose monocaprate, sucrose monochorate, and the like. Among these, dodecyl-D-maltoside, sucrous monolaurate, and oxatridecyl-D-mannoside are preferable. The concentration of surfactant (a) in the buffer solution is, for example, 0.001 to 1 wt %, preferably 0.005 to 0.05 wt %, and more preferably 0.01 to 0.03 wt %.

The material for the capillary tube is not particularly limited. Examples thereof include glass, fused silica, and plastic. The inner wall of a capillary tube made of glass or fused silica usually has negative electric charges. The inner wall of a capillary tube made of plastic has positive or negative electric charges, or is uncharged (nonpolar), depending on the presence or absence of and the type of polar group contained in the plastic. Even in the case of a plastic having no polar group, the introduction of a polar group allows it to have an electric charge. A commercially available product may be used as the capillary tube made of plastic, and examples thereof include those formed of polymethylmethacrylate, polycarbonate, polystyrene, polyethylene, polytetrafluoroethylene (PTFE), polyether ether ketone (PEEK), and the like. The inner diameter of the capillary tube is, for example, 10 to 200 μm, and preferably 25 to 100 μm. The length of the capillary tube is, for example, 10 to 1000 mm.

In the present invention, the inner wall of the capillary tube may be coated with a cationic group-containing compound. As the cationic group-containing compound, for example, a compound containing the cationic group and a reaction group may be used. In the case where the capillary tube is made of glass or fused silica, a compound (a silylation agent) containing the cationic group and silicon may be used. Preferable examples of the cationic group include an amino group and an ammonium group. Further, preferable examples of the cationic group-containing compound include a silylation agent that contains at least one cationic group that is an amino group or an ammonium group. The amino group may be a primary amino group, a secondary amino group, or a tertiary amino group.

Examples of the silylation agent include N-(2-diaminoethyl)-3-propyltrimethoxysilane, aminophenoxydimethylvinylsilane, 3-aminopropyldiisopropylethoxysilane, 3-aminopropylmethylbis(trimethylsiloxy)silane, 3-aminopropylpentamethyldisiloxane, 3-aminopropylsilanetriol, bis(P-aminophenoxy)dimethylsilane, 1,3-bis(3-aminopropyl)tetramethyldisiloxane, bis(dimethylamino)dimethylsilane, bis(dimethylamino)vinylmethylsilane, bis(2-hydroxyethyl)-3-aminopropyltriethoxysilane, 3-cyanopropyl(diisopropyl)dimethylaminosilane, (aminoethylaminomethyl)phenethyltrimethoxysilane, N-methylaminopropyltriethoxysilane, tetrakis(diethylamino)silane, tris(dimethylamino)chlorosilane, tris(dimethylamino)silane, and the like.

An agent obtained by substituting silicon with titanium or zirconium in the silylation agent may be used. The silylation agents may be used alone or in a combination of two or more types.

The inner wall of a capillary tube is coated using the silylation agent, for example, as follows. First, the silylation agent is dissolved or dispersed in an organic solvent; thereby preparing a treatment liquid. The organic solvent used for preparing the treatment liquid can be, for example, dichloromethane or toluene. The concentration of the silylation agent in the treatment liquid is not particularly limited. This treatment liquid is passed through a capillary tube made of glass or fused silica and is heated. This heating allows the silylation agent to be bonded to the inner wall of the capillary tube by a covalent bond. As a result, the cationic group is placed on the inner wall of the capillary tube. Thereafter, it is washed (subjected to aftertreatment) with at least one of an organic solvent (e.g., dichloromethane, methanol, or acetone), an acid solution (e.g., phosphoric acid), an alkaline solution, and a surfactant solution. Preferably, this washing is carried out, although it is optional. A commercially available product may be used as the capillary tube having an inner wall coated with a silylation agent.

Next, the electrophoresis step of carrying out electrophoresis of the sample is performed by introducing the sample into the buffer solution in the capillary tube, and applying a voltage across both ends of the capillary tube. The electrophoresis step can be performed, for example, as follows.

First, a buffer solution containing an anionic group-containing compound such as chondroitin sulfate is passed through the capillary tube under pressure applied by, for example, a pump. The time during which it is passed therethrough is, for example, 1 to 60 minutes and the pressure applied when it is passed therethrough is, for example, 0.05 to 0.1 MPa. Electrophoresis is carried out by introducing the hemoglobin sample into the buffer solution in a state where the buffer solution is present in the capillary tube, and applying a voltage across both ends of the capillary tube. The sample is introduced into the capillary tube from the anode side thereof. The hemoglobin in the thus introduced sample forms a complex by being bonded with the anionic group-containing compound in the buffer solution. The application of a voltage generates an electroosmotic flow in the buffer solution contained in the capillary tube and, thereby, the complex migrates toward the cathode side of the capillary tube. The voltage applied is, for example, on the order of 1 to 30 kV. This migration is detected by an optical method. Such detection made by the optical method is not particularly limited. Preferably, it is carried out at a wavelength of 415 nm.

When electrophoresis is carried out following at least one of the modes (A) and (B) as described above, HbA0 and HbS can be separated by the action of at least one of the surfactants (a) and (b).

In the present invention, the hemoglobin that is to be analyzed is not particularly limited. Examples thereof include normal hemoglobin (HbA0), glycated hemoglobin (e.g., HbA1c, labile HbA1c, GHbLys), genetic variants of hemoglobin (e.g., HbS, HbC, HbM, HbH), HbF, and the like.

EXAMPLES

Next, examples of the present invention will be described together with comparative examples.

Example 1-1

A capillary tube (with an overall length of 32 cm, an effective length of 8.5 cm, and an inner diameter of 50 μm) made of fused silica was provided. Furthermore, a buffer solution (pH 4.8) was provided that contained chondroitin sulfate C added to 100 mM fumaric acid and an aqueous arginine acid solution at a ratio of 0.8 wt %. To this buffer solution, surfactant (a) (dodecyl-D-maltoside, number of carbon atoms in alkyl group: 12) was added at a ratio of 0.02 wt %. The buffer solution to which surfactant (a) had been added was passed through the capillary tube under a pressure of 0.1 MPa (1000 mbar). With the capillary tube being filled with the buffer solution, a sample containing hemoglobin dissolved in purified water was injected into the capillary tube. Thereafter, a voltage of 10 kV was applied across both ends of the capillary tube; thereby, electrophoresis was carried out. The hemoglobin sample was injected into the capillary tube from the anode side thereof. The hemoglobin that had migrated was detected at an absorbance of 415 nm. Here, as the sample, two types of samples consisting of a sample containing HbS and a sample not containing HbS were provided, and each of them was subjected to electrophoresis. The results are shown in the electropherograms in FIG. 1. In FIG. 1, the electropherogram of the sample not containing HbS is indicated by the dotted line, and the electropherogram of the sample containing HbS is indicated by the thick solid line. As shown in FIG. 1, in this example, HbA0 and HbS could be detected separately. Furthermore, detection could be performed within a period of time as short as 6 minutes.

Example 1-2

Figure 2:
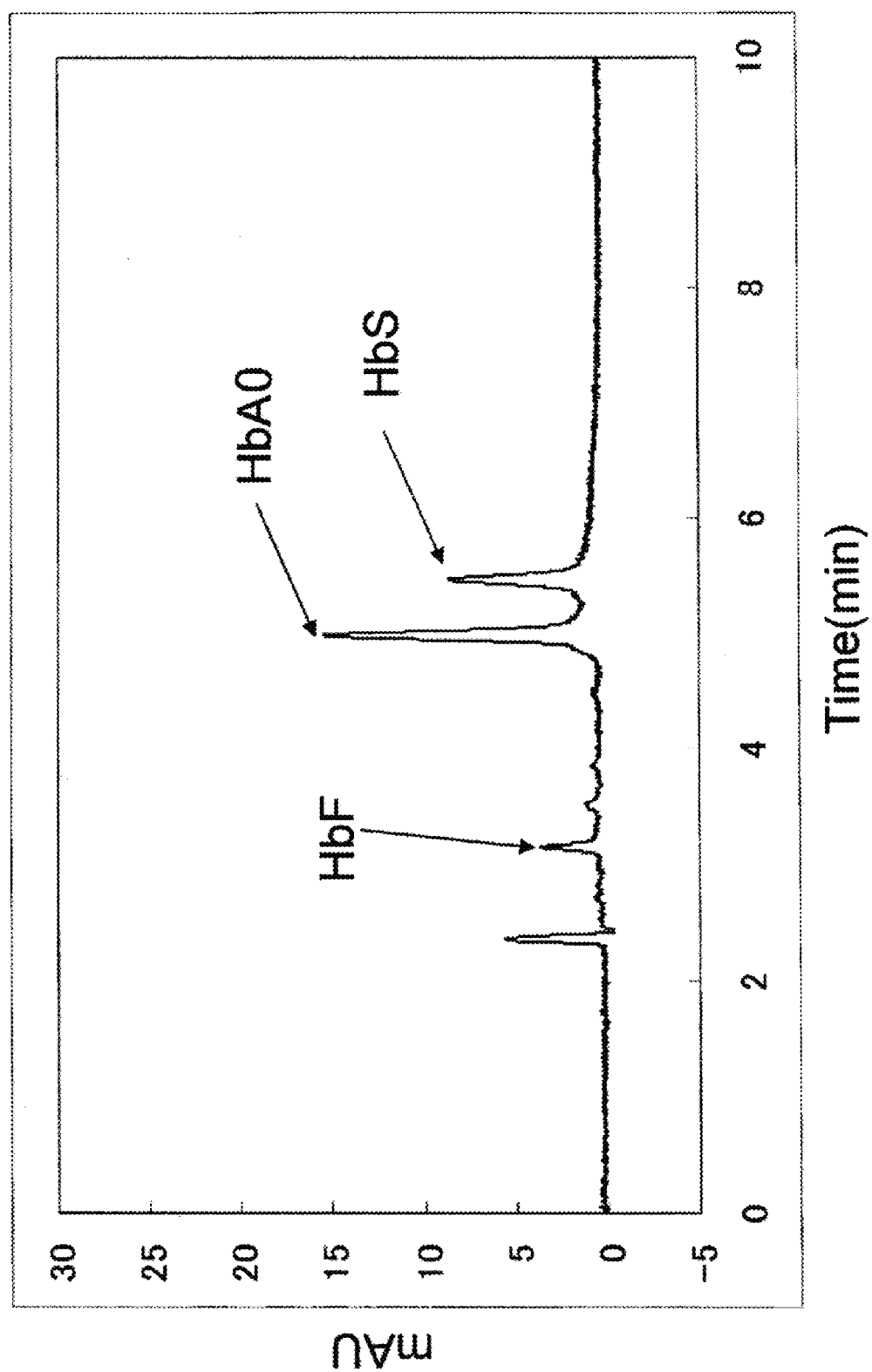
FIG. 2 shows an electropherogram showing the results of an analysis of hemoglobin in another example of the present invention.

As surfactant (a), sucrose monolaurate (number of carbon atoms in alkyl group: 11) was used instead of dodecyl-D-maltoside. Furthermore, as the sample, only a sample containing HbS was provided and subjected to electrophoresis. Capillary electrophoresis was carried out as in Example 1-1 except for the above. The results are shown in the electropherogram in FIG. 2. As shown in FIG. 2, in this example, HbA0 and HbS could be detected separately. Furthermore, detection could be performed within a period of time as short as 6 minutes.

Example 1-3

Figure 3:
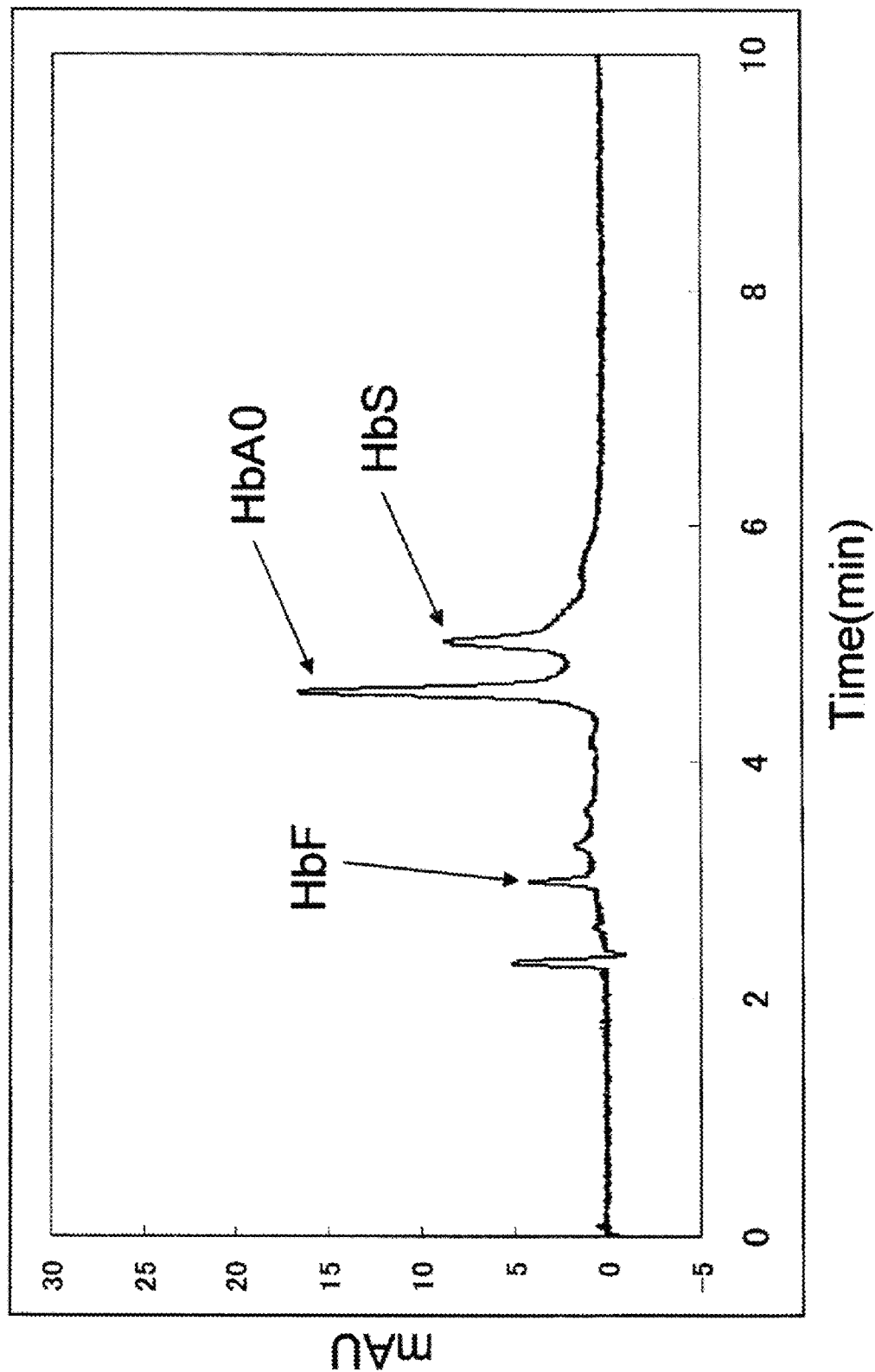
FIG. 3 shows an electropherogram showing the results of an analysis of hemoglobin in yet another example of the present invention.

As surfactant (a), oxatridecyl-D-mannoside (number of carbon atoms in alkyl group: 12) was used instead of dodecyl-D-maltoside. Furthermore, as the sample, only a sample containing HbS was provided and subjected to electrophoresis. Capillary electrophoresis was carried out as in Example 1-1 except for the above. The results are shown in the electropherogram in FIG. 3. As shown in FIG. 3, in this example, HbA0 and HbS could be detected separately. Furthermore, detection could be performed within a period of time as short as 6 minutes.

Example 1-4

Figure 4:
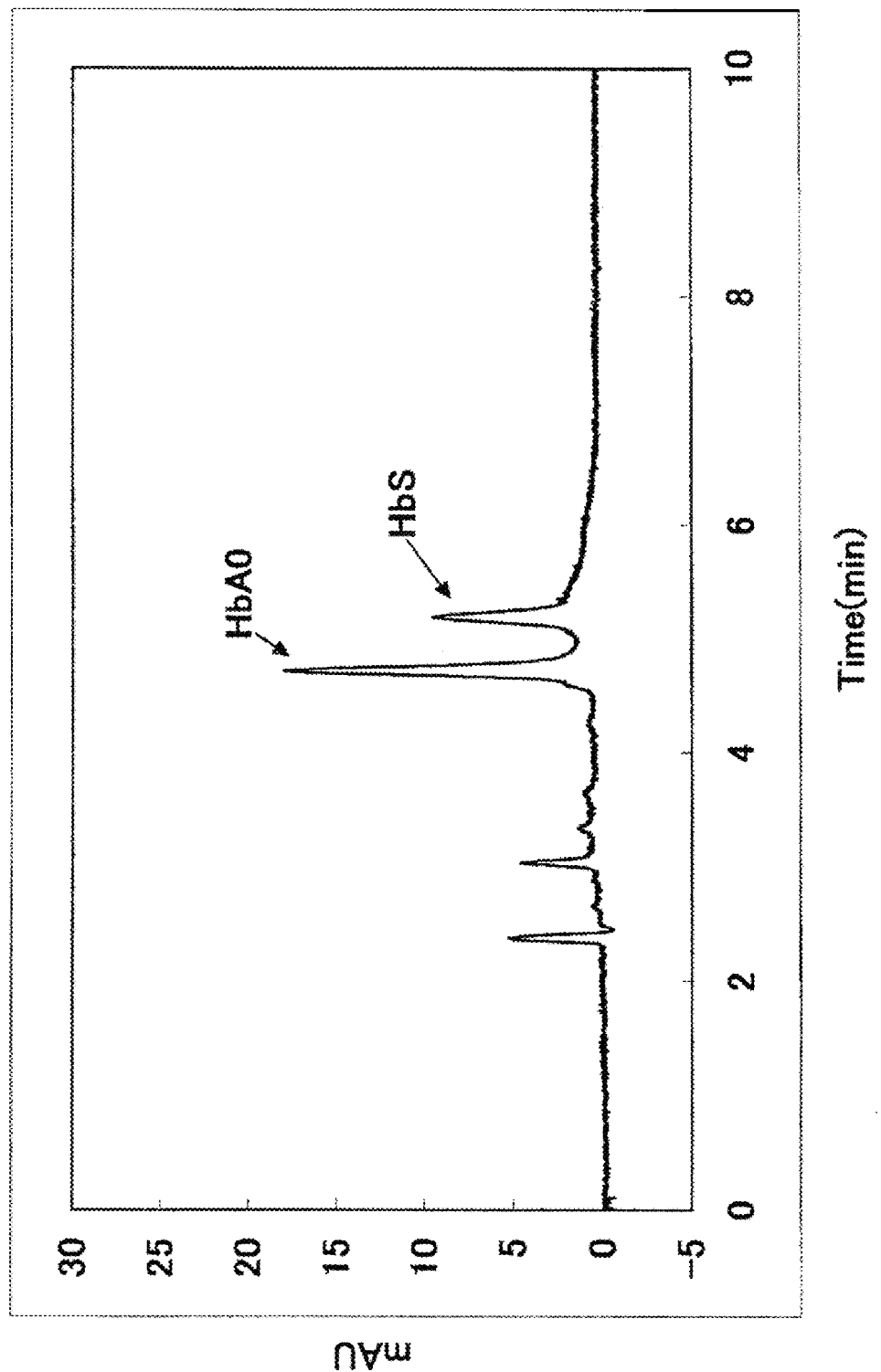
FIG. 4 shows an electropherogram showing the results of an analysis of hemoglobin in yet another example of the present invention.

As surfactant (a), undecyl-maltoside (number of carbon atoms in alkyl group: 11) was used instead of dodecyl-D-maltoside. Furthermore, as the sample, only a sample containing HbS was provided and subjected to electrophoresis. Capillary electrophoresis was carried out as in Example 1-1 except for the above. The results are shown in the electropherogram in FIG. 4. As shown in FIG. 4, in this example, HbA0 and HbS could be detected separately. Furthermore, detection could be performed within a period of time as short as 6 minutes.

Example 1-5

Figure 5:
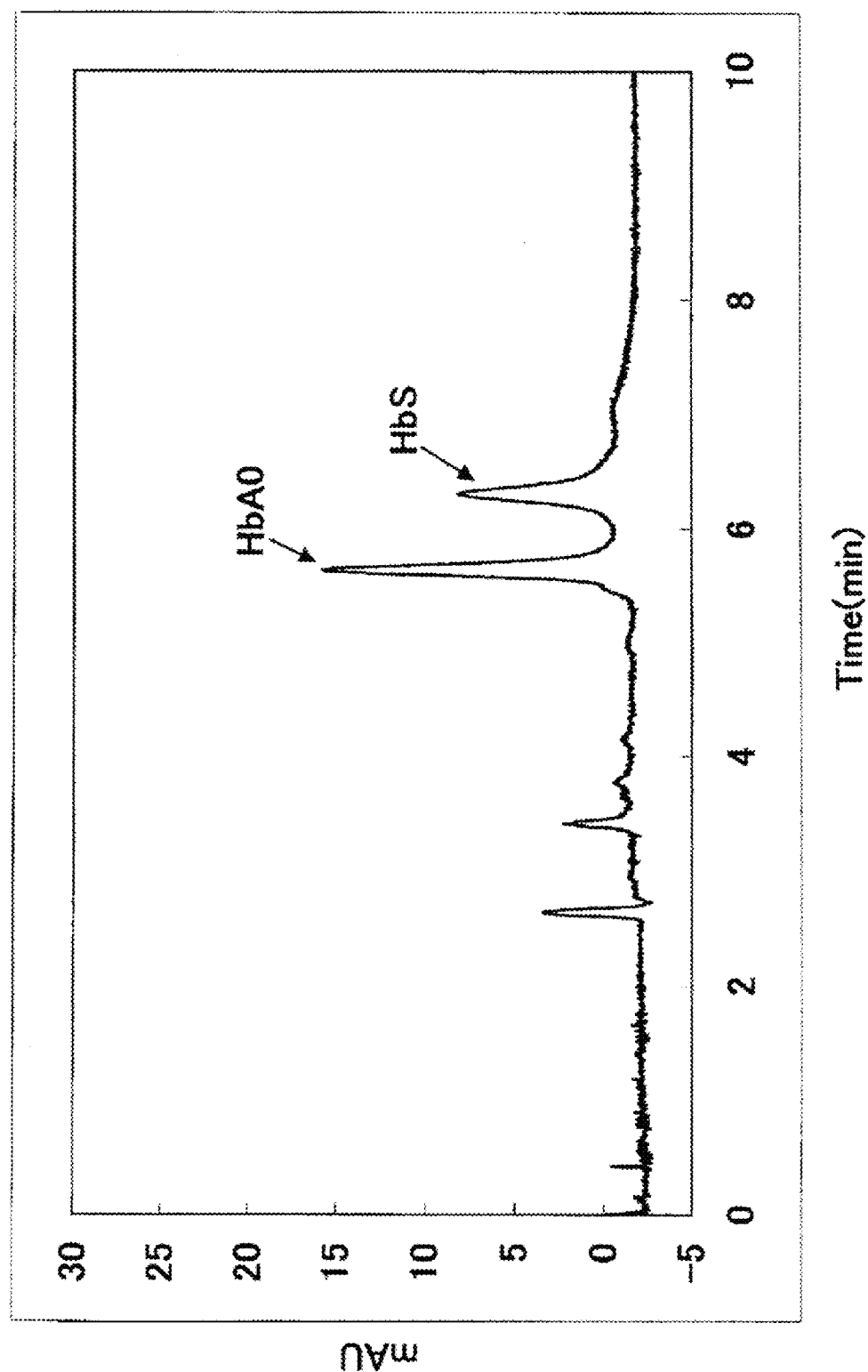
FIG. 5 shows an electropherogram showing the results of an analysis of hemoglobin in yet another example of the present invention.

To the buffer solution, hexadecyl-maltoside (number of carbon atoms in the alkyl group: 16) was added at a ratio of 0.005 wt % instead of dodecyl-D-maltoside added at a ratio of 0.02 wt %. Furthermore, as the sample, only a sample containing HbS was provided and subjected to electrophoresis. Capillary electrophoresis was carried out as in Example 1-1 except for the above. The results are shown in the electropherogram in FIG. 5. As shown in FIG. 5, in this example, HbA0 and HbS could be detected separately. Furthermore, detection could be performed within a period of time as short as 7 minutes.

Comparative Example 1-1

Figure 6:
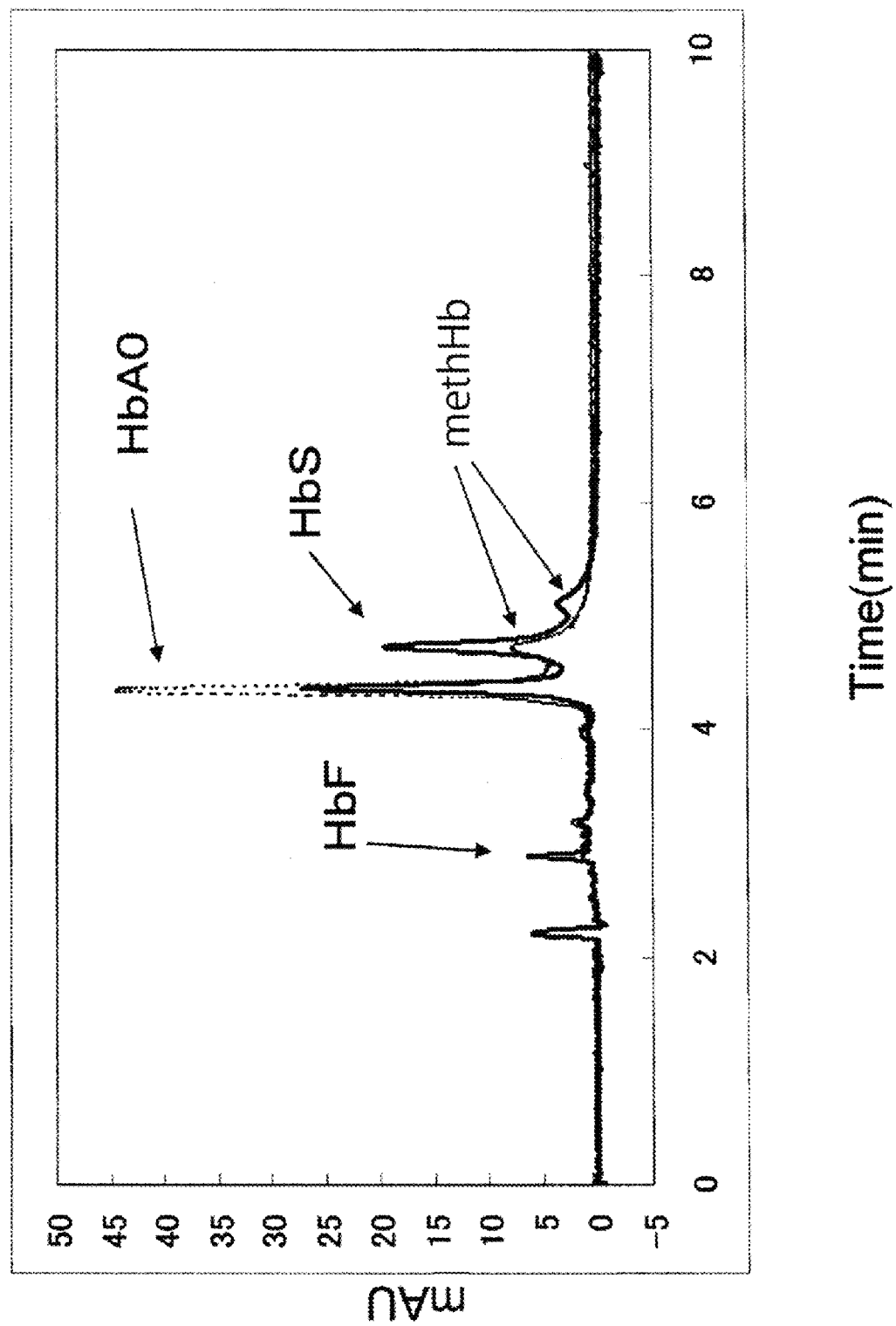
FIG. 6 shows electropherograms showing the results of an analysis of hemoglobin in a comparative example.

Capillary electrophoresis was carried out as in Example 1-1, except that surfactant (a) was not used. The results are shown in the electropherograms in FIG. 6. In FIG. 6, the electropherogram of the sample not containing HbS is indicated by the dotted line, and the electropherogram of the sample containing HbS is indicated by the thick solid line. As shown in FIG. 6, in this comparative example, the peaks of methHb and HbS overlap, and HbA0 and HbS could not be detected separately.

Comparative Example 1-2

Figure 7:
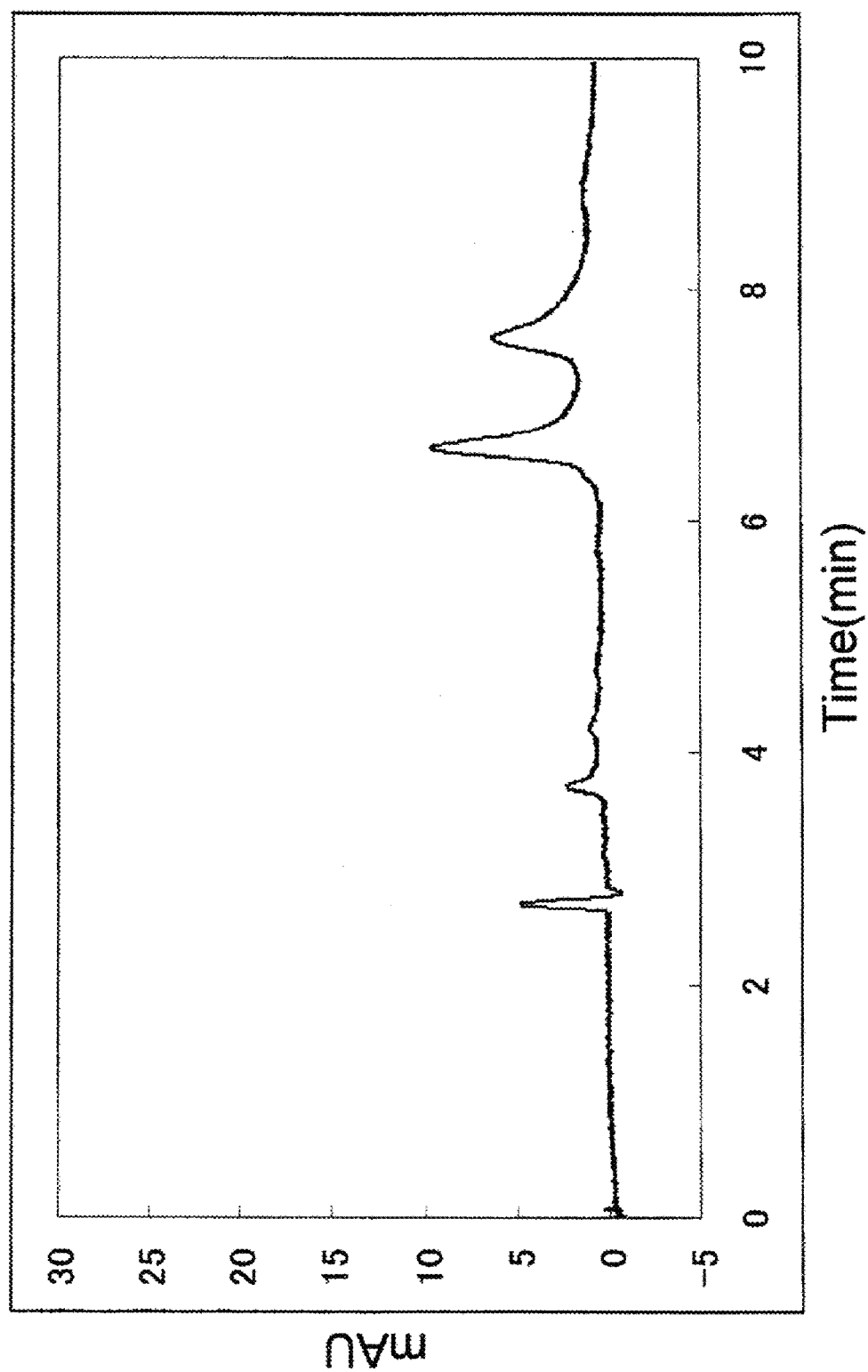
FIG. 7 shows an electropherogram showing the results of an analysis of hemoglobin in another comparative example.

As surfactant (a), Triton X-100 (brand name: manufactured by Nacalai Tesque, Inc.) was used instead of dodecyl-D-maltoside. Furthermore, as the sample, only a sample containing HbS was provided and subjected to electrophoresis. The capillary electrophoresis was carried out as in Example 1-1 except for the above. The results are shown in the electropherogram in FIG. 7. As shown in FIG. 7, in this comparative example, Hb was detected at a later point in time, the peak width was increased, and HbA0 and HbS could not be detected separately.

Example 2-1 and Comparative Example 2-1

Figure 8:
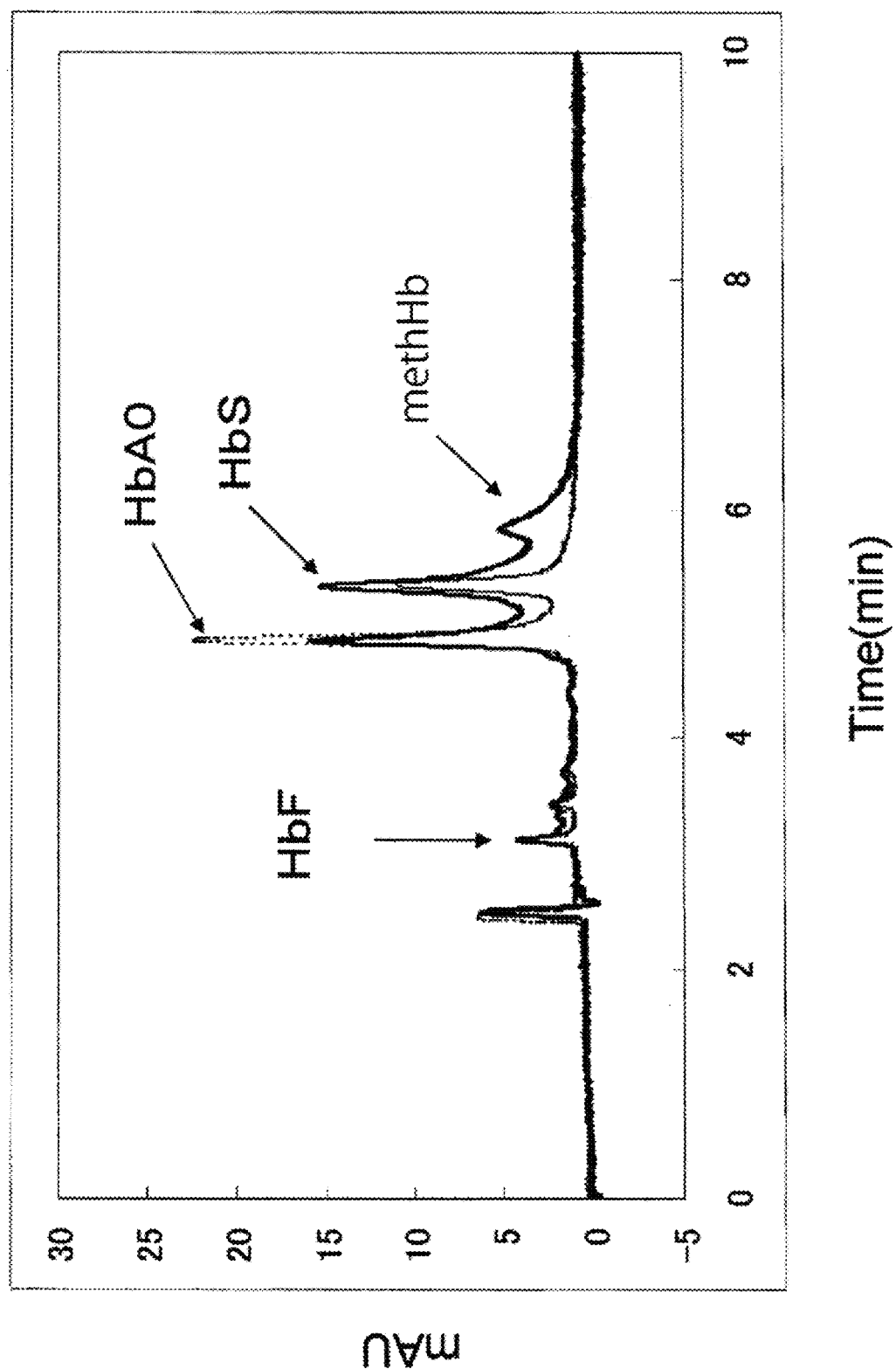
FIG. 8 shows electropherograms showing the results of an analysis of hemoglobin in yet another example of the present invention.

A capillary tube (with an overall length of 32 cm, an effective length of 8.5 cm, and an inner diameter of 50 μm) made of fused silica was provided as in Example 1. Furthermore, a buffer solution (pH 4.8) that contained chondroitin sulfate C added to 100 mM fumaric acid and an aqueous arginine acid solution at a ratio of 0.8 wt % was provided. The buffer solution was passed through the capillary tube under a pressure of 0.1 MPa (1000 mbar). Furthermore, a sample containing hemoglobin (including HbS) dissolved in purified water was provided. To this sample, surfactant (b) (palmityl sulfobetaine; brand name SB16, manufactured by Sigma) was added at a ratio of 0.1 wt %. With the capillary tube being filled with the buffer solution, the sample was injected into the capillary tube. Thereafter, a voltage of 10 kV was applied across both ends of the capillary tube; thereby, electrophoresis was carried out. The hemoglobin sample was injected into the capillary tube from the anode side thereof. The hemoglobin that had migrated was detected at an absorbance of 415 nm. Here, as Comparative Example 2-1, a sample to which the surfactant (b) had not been added was also subjected to electrophoresis in a similar manner. The results are shown in the electropherograms in FIG. 8. In FIG. 8, the electropherogram of the sample containing surfactant (b) (Example 2-1) is indicated by the dotted line, and the electropherogram of the sample not containing surfactant (b) (Comparative Example 2-1) is indicated by the thick solid line. As shown in FIG. 8, in Example 2-1, HbA0 and HbS could be detected separately, and detection could be performed within a period of time as short as 6 minutes. On the other hand, in Comparative Example 2-1, HbA0 and HbS could not be detected separately.

Comparative Example 2-2

Figure 9:
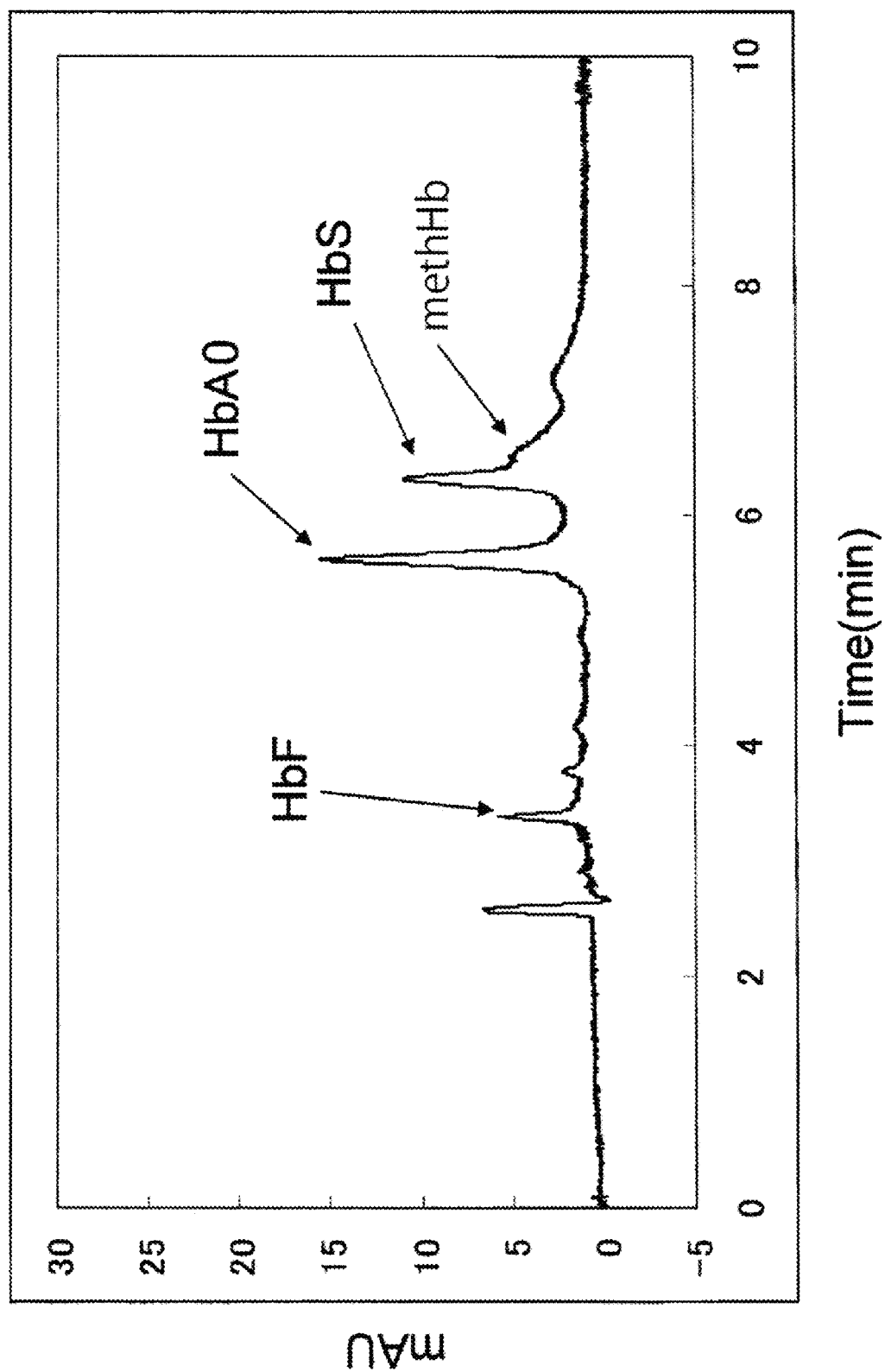
FIG. 9 shows an electropherogram showing the results of an analysis of hemoglobin in yet another comparative example.

As surfactant (b), dodecyl-D-maltoside was used instead of palmityl sulfobetaine. Capillary electrophoresis was carried out as in Example 2-1 except for the above. The results are shown in the electropherogram in FIG. 9. As shown in FIG. 9, in this comparative example, methHb could be detected at a later point in time, but HbA0 and HbS could not be detected separately.

Comparative Example 2-3

Figure 10:
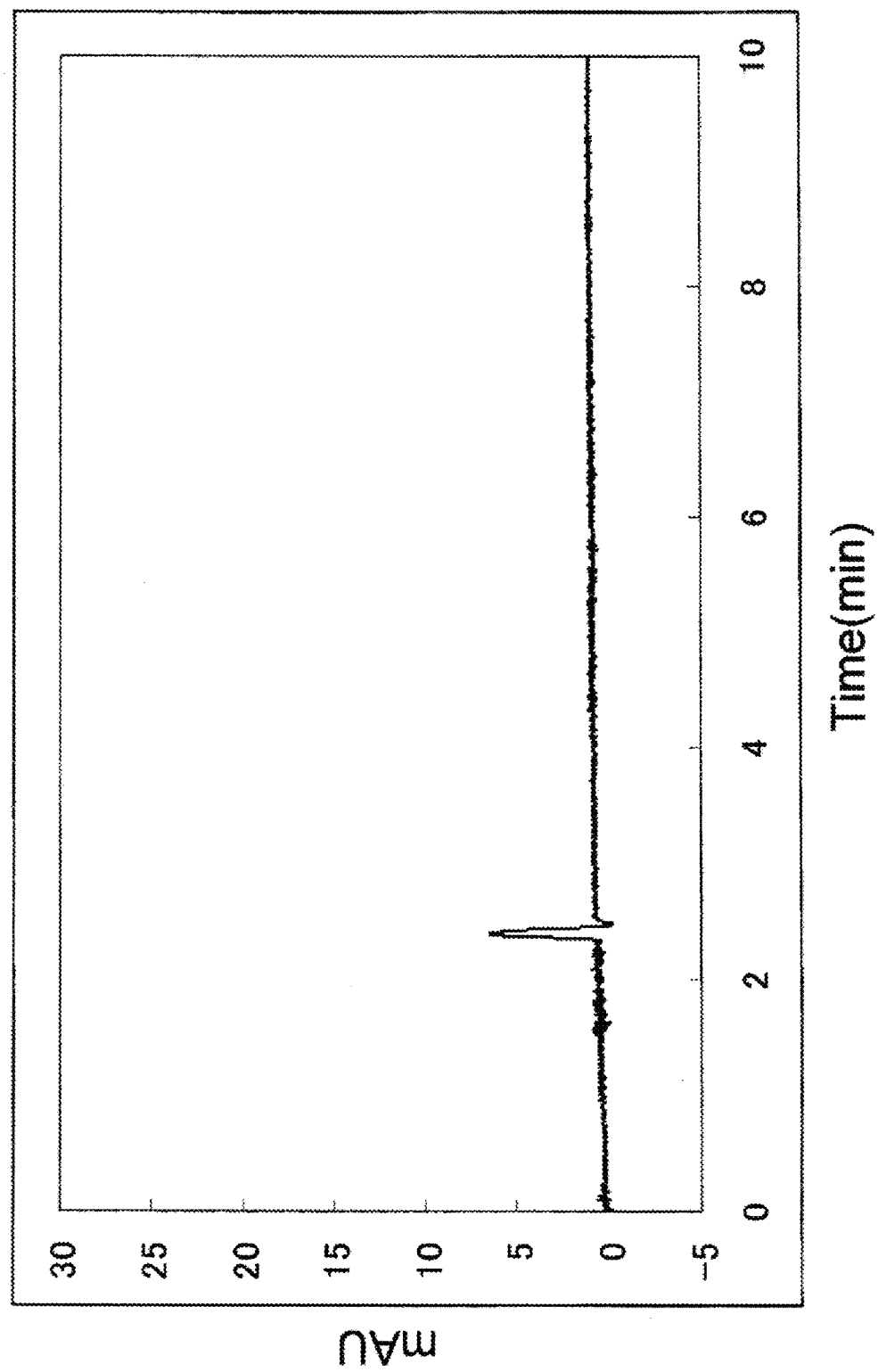
FIG. 10 shows an electropherogram showing the results of an analysis of hemoglobin in yet another comparative example.

As surfactant (b), Triton X-100 was used instead of palmityl sulfobetaine. Capillary electrophoresis was carried out as in Example 2-1 except for the above. The results are shown in the electropherogram in FIG. 10. As shown in FIG. 10, in this comparative example, Hb could not be detected.

INDUSTRIAL APPLICABILITY

As described above, methods for analyzing hemoglobin by capillary electrophoresis of the present invention are methods that allow the apparatus to be smaller in size, allow a highly precise analysis to be obtained, and allow the analysis to be performed in a short period of time. The present invention is applicable to all fields where hemoglobin is analyzed, such as laboratory tests, biochemical examinations, and medical research. The intended use thereof is not limited and it is applicable to a wide range of fields.

The invention claimed is:
1. A method for analyzing hemoglobin by a capillary electrophoresis method, comprising:
a sample-providing step of providing a sample containing hemoglobin;
a capillary tube-providing step of providing a capillary tube containing a buffer solution; and
an electrophoresis step of carrying out electrophoresis of the sample, by introducing the sample into the buffer solution of the capillary tube, and applying a voltage across both ends of the capillary tube;
wherein the hemoglobin is HbA1c and is analyzed following at least one of modes (A) and (B) below:
(A) the electrophoresis is carried out with the capillary tube filled with the buffer solution to which a surfactant (a) has been added in the range of 0.005 to 0.05 wt % by causing the buffer solution to pass through the capillary tube in the capillary tube-providing step, by injecting the sample into the capillary tube with the capillary tube being filled with the buffer solution, the surfactant (a) being a non-ionic surfactant having an alkyl group as a hydrophobic portion and a sugar as a hydrophilic portion;
(B) the electrophoresis is carried out with a surfactant (b) added to the sample in the range of 0.001 to 0.1 wt % in the sample-providing step and the capillary tube filled with the buffer solution by causing the buffer solution to pass through the capillary tube in the capillary tube-providing step, by injecting the sample into the capillary tube with the capillary tube being filled with the buffer solution, the surfactant (b) being a betaine-type amphoteric surfactant; and
wherein HbA0 and HbS are separated.

2. The analytical method according to claim 1, wherein, in the mode (A), the surfactant (a) is added to the buffer solution in the capillary tube-providing step.

3. The analytical method according to claim 1, wherein, in the surfactant (a), the alkyl group has 11 to 16 carbon atoms, and the sugar is a monosaccharide or a disaccharide.

4. The analytical method according to claim 1, wherein, in the surfactant (a), the alkyl group is a linear alkyl group having 11 or 12 carbon atoms, and the sugar is a disaccharide.

5. The analytical method according to claim 1, wherein, in the mode (B), the surfactant (b) is added to the sample in the sample-providing step.

6. The analytical method according to claim 1, wherein the surfactant (b) is a sulfobetaine-type amphoteric surfactant.

7. The analytical method according to claim 1, wherein an anionic group-containing compound is added to the buffer solution, and a complex of the hemoglobin HbA1c and the anionic group-containing compound is subjected to electrophoresis.

8. The analytical method according to claim 7, wherein the anionic group-containing compound is added to the buffer solution in the capillary tube-providing step.

9. The analytical method according to claim 7, wherein the anionic group-containing compound is an anionic group-containing polysaccharide.

* * * * *